United States Patent [19]

Liu et al.

[11] Patent Number: 5,374,545
[45] Date of Patent: Dec. 20, 1994

[54] **CELL WALL LYTIC ENZYMES FROM *BACILLUS PABULI***

[75] Inventors: Chi-Li Liu, Davis, Calif.; Janet M. Overholt, Danbury, Conn.

[73] Assignee: Novo Nordisk A/S, Bagsvaerd, Denmark

[21] Appl. No.: 86,388

[22] Filed: Jul. 1, 1993

Related U.S. Application Data

[63] Continuation of Ser. No. 341,854, Apr. 24, 1989, abandoned.

[51] Int. Cl.$^5$ .................. C12N 9/00; C12N 1/20; C12N 1/00
[52] U.S. Cl. ................. 435/183; 435/252.31; 435/832; 435/195; 435/206; 435/221
[58] Field of Search .......... 435/200, 206, 183, 252.31, 435/832, 221, 195, 206

[56] References Cited

U.S. PATENT DOCUMENTS

| | | | |
|---|---|---|---|
| 3,816,260 | 6/1974 | Sugiyama | 435/206 |
| 4,032,663 | 6/1977 | Kobayashi et al. | 435/200 |

FOREIGN PATENT DOCUMENTS

8043757  11/1980  Japan .

OTHER PUBLICATIONS

Suzuki et al., Agric. Biol. Chem., 1985, 49(6), pp. 1719–1726.
Saint-Blancard et al., BioSci. Rep., 1981, 1(2), pp. 119–123.
Selyavko, Nek. Aspekty, Fiziol. Mikroorg., 1983, 51–4 (Russ.), Edited by Gaziev, A.
Beyek et al., Appl. Microbiol. Biotechnol., 1985, 23, pp. 140–146.
Suzuki et al., Agric. Biol. Chem., 1985, 49(10), 3049–50.
Hansen et al, *Distribution of . . .* , Applied and Envir. Micro., Apr. 1985, pp. 1019–1021, vol. 49, No. 4.
Nakamura, *Bacillus alginolyticas*, Int. Jor. of Sys. Bacter., vol. 37, No. 3, pp. 284–286, 1987.
Alexander et al, *Bacillus glucanolyticus*, Int. Jour. of Syst. Bact., vol. 39, No. 2, pp. 112–115, 1989.
Journal of Bacteriology, May 1970, pp. 347–350, Martin et al., V. 102, N. 2.
Int'l. J. of Systematic Bacteriology, Apr. 1984, p. 224–226, V. 34, N. 2, Nakamura.
J. of Bacteriology, Feb. 1966, vol. 91, No. 2, Ensign et al.
J. Ferment. Technol., vol. 53, No. 10, p. 703–712, 1975, Yoshimoto et al.

*Primary Examiner*—David M. Naff
*Assistant Examiner*—Michael V. Meller
*Attorney, Agent, or Firm*—Steve T. Zelson; Elias J. Lambiris

[57] ABSTRACT

A bacteriolytic enzyme complex is obtained from a bacterial culture of *Bacillus pabuli* strains, e.g., isolates 350-2 (NRRL B-18446) and 391-1 (NRRL B-18447). This bacteriolytic enzyme complex is useful as an antibacterial agent against both Gram-positive and Gram-negative bacteria. The enzyme complex may be produced by cultivating the *B. pabuli* microorganisms in an aqueous medium containing cornsteep liquor, after which the lyric enzyme complex can be recovered from the fermentation broth.

4 Claims, 1 Drawing Sheet

CELL WALL LYTIC ENZYMES FROM *BACILLUS PABULI*

This application is a continuation application of co-pending application Ser. No. 07/341,854, filed Apr. 24, 1989, now abandoned.

The present invention relates to novel lytic enzyme complexes, to the process for preparing said enzymes, and to the use of these enzymes as growth inhibition or antibacterial agents. These complexes are capable of hydrolyzing bacterial cell walls especially those of important Gram-negative bacteria such as *E. coli* (e.g., ATCC 26), *Pseudomonas aeruginosa* (e.g., ATCC 9027), *Salmonella arizona* (e.g., ATCC 12323) and *Vibrio parahaemolyticus* (e.g., ATCC 35117).

BACKGROUND OF INVENTION

Gram-negative bacteria are ubiquitous, some of them such as *Pseudomonas aeruginosa* and *Vibrio parahaemolyticus* are pathogenic, Enzymes capable of depolymerizing bacterial cell walls may be used to control or prevent the growth of target microorganisms such as those listed above. Lytic enzymes of this sort are much to be desired, and have long been sought, for the most part without success.

Most of the numerous bacterial cell wall degrading enzymes known to the art lyse only Gram-positive bacteria, not Gram-negative bacteria.

The surface structure of Gram-negative bacteria is exceedingly complex. An inner layer composed of peptidogliycan is enclosed by an outer layer of mostly lipopolysaccharide, lipoprotein, and lipid (C. A. Schnaitman, J. Bacteriol. 1971. 108:553 and H. D. Heilman, Eur. J. Biochem. 1972. 31:456). The multiple-track layers of the bacteria surface function as a barrier which prevents most llytic enzymes from reaching the underlying peptidoglycan (J. M. Ghuysen, Bacteriol. Rev. 1968. 32:425).

The inventors hereof are aware of three known in the art lytic enzymes that lyse Gram-negative bacteria (S. Murano et. al., Agric. Biol. Chem. 1974. 38:2305, T. Yoshimoto et. al., J. Ferment. Technol. 1975. 53:703 and K. Suzuki. et. al., Agric. Biol. Chem. 1985. 49:1719). These enzymes have been identified as a N-acetylglucosaminidase, N-acetytmuramidase and an endopeptidase of serine protease type, respectively.

Bacteriolytic enzymes with capability for hydrolyzing both Gram-positive and many Gram-negative bacteria, e.g., *Vibrio parahaemolyticus* and *Salmonella arizona* have not been known heretofore.

SUMMARY OF INVENTION

It has now been discovered that strains of Bacillus pabuli elaborate extracellular enzyme complexes capable of hydrolyzing the cell walls of many Gram-positive and Gram-negative microorganisms, including for example *E. coli, Pseudomonas aeruginosa, Serratia marcescens, Corynebacterium liquefaciens* and *Micrococcus luteus*. These bacteriolytic enzyme complexes (also termed lytic enzyme complexes) may be used to inhibit bacterial growth and/or lyse an existing bacteria population, e.g., by applying at least about 100 units per ml of the complex to the target being protected, preferably, at least, about 500 units/mi.

These enzyme complexes are useful antibacterial agents for various applications including health care and food industry applications.

The present invention comprises the *B. pabuli* bacteriolytic enzyme complexes, their methods of use, and the process for preparing the enzymes.

DISCUSSION OF THE INVENTION

Use of the bacteriolytic enzyme complexes of this invention as antibacterial agents are discussed below principally with reference to their usage in the food industry, such emphasis upon this particular preferred mode of use being a convenient way to provide an explanation of the invention as a whole. However, it should be understood that the bacteriolytic enzyme complexes of this invention may be used elsewhere than the food industry for their lytic action. For example, to name a minor use important to biologic research, the lytic enzyme complexes may be used as cell-opening aids to facilitate protoplasting of both Gram-positive and Gram-negative organisms.

For a lytic enzyme complex to be useful in the food industry as an antibacterial agent, the enzyme complex must be capable of degrading a broad spectrum of bacteria and in particular microorganisms which cause food spoilage and the foodborne pathogen microorganisms. Many bacteriolytic enzymes heretofore known, e.g., AL-1 enzyme from Myxobacter (J. C. Ensign et. el., J. Bacteriol. 1966. 91:524) and Mutanolysin (from *Streptomyces globisporus*) are inactive toward some Gram-negative bacteria of interest to the food industry such as *Serratia marcescens, P. aeruginosa* and *E coli*, all of which the lytic enzyme complexes of this invention can lyse.

Parenthetically, it is noted that known Gram-negative bacteria lysing enzymes such as 152-enzyme from Micromonospora sp. (K. Suzuki, et. al., Agric. Biol. Chem. 1985. 49:1719) and *Pseudomonas aeruginosa*—lytic enzyme from *Streptomyces griseus* P-51 (T. Yoshimoto, et. al., J. Ferment. Technol. 1975. 53:703) have narrower target organism spectra than the bacteriollytic enzyme complexes of this invention.

Microbial Source

The bacteriollytic enzyme complexes of this invention are elaborated extracellularly by all strains of *Bacillus pabuli* known to the inventors hereof. Two lytic enzyme complex producing strains have been isolated by the inventors hereof, i.e., *Bacillus pabuli* strain 350-2 (NRRL B-18446) and *Bacillus pabuli* strain 391-1 (NRRL B-18447); both strains secrete the bacteriolytic enzyme complexes of this invention. In addition, the type strain for *Bacillus pabuli*, strain NRS-924, was obtained from the Northern Regional Research Center of U.S.D.A., Peoria, Ill., and found also to produce a bacteriollytic enzyme complex of this invention. For example, each llytic enzyme complex is active against *E coli*. The type strain, designated NRRL NRS-924 has been described by L. K. Nakamura, Int. J. of Systematic Bacter. April 1984. 34:224.

The crude llytic enzyme complex produced by *Bacillus pabuli* strain 391-1 showed a pH optimum of 6.0 and a temperature optimum of 50°–60° C. when *Pseudomonas aeruginosa* was used as the substrate. Changes in ionic strength of the reaction buffer affect the activity of the lytic enzyme complexes. The optimal ionic strength was determined for the complex produced by isolate 391-1 as 20 mM phosphate buffer, pH 7.0.

As may be expected in the instance of an enzyme complex, each of the different strains of *Bacillus pabuli* available as of the date hereof produce an individually differing lytic enzyme complex, the difference from one lytic enzyme complex to another lytic enzyme complex being due at least in part to variation in the content of the individual enzyme activities present in the lytic enzyme complexes. As may be expected, the enzyme complex from each of the different *B. pabuli* strains is either more or less effective one than the other against individual (i.e., pure culture) test microorganisms. However, each of the lytic enzyme complexes was found to be effective to a significant degree against all of the test target microorganisms, and the test organism list included some known troublesome Gram-negative bacteria, see the Table I hereinafter.

According to a further aspect of this invention there is provided a method for producing the lytic enzyme complexes, which process is characterized by cultivation of a lytic enzyme producing strain of *Bacillus pabuli* under aerobic conditions in a nutrient medium containing assimilable sources of carbon, nitrogen, and phosphorus, followed by recover of the extracellularly produced lytic enzyme complex from the fermentation broth. Aerobic growth conditions and nutrients known to the art for *Bacillus pabuli* may be employed. Submerged fermentation is preferred.

DETAILED DESCRIPTION OF THE INVENTION

Figure 1:
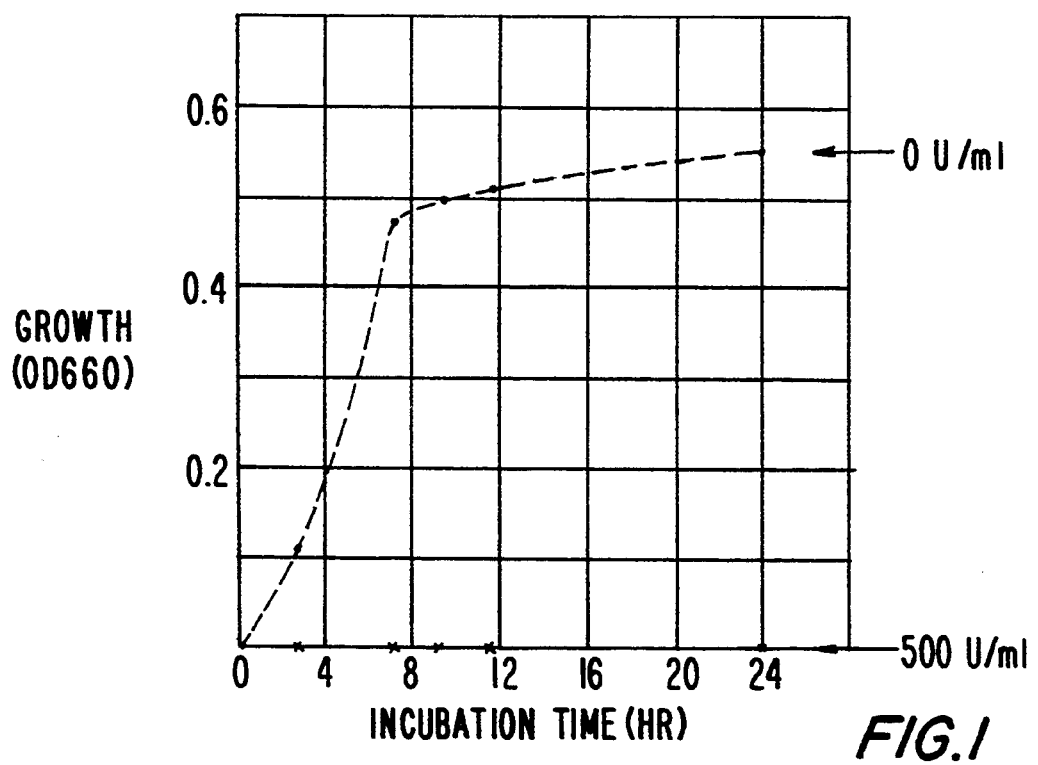

For further understanding of this invention, reference is made to the attached drawings wherein:

FIG. 1 graphically presents the inhibitory effect of lytic enzyme from strain 391-1 on the growth of *E. coli* (ATCC 26).

Figure 2:
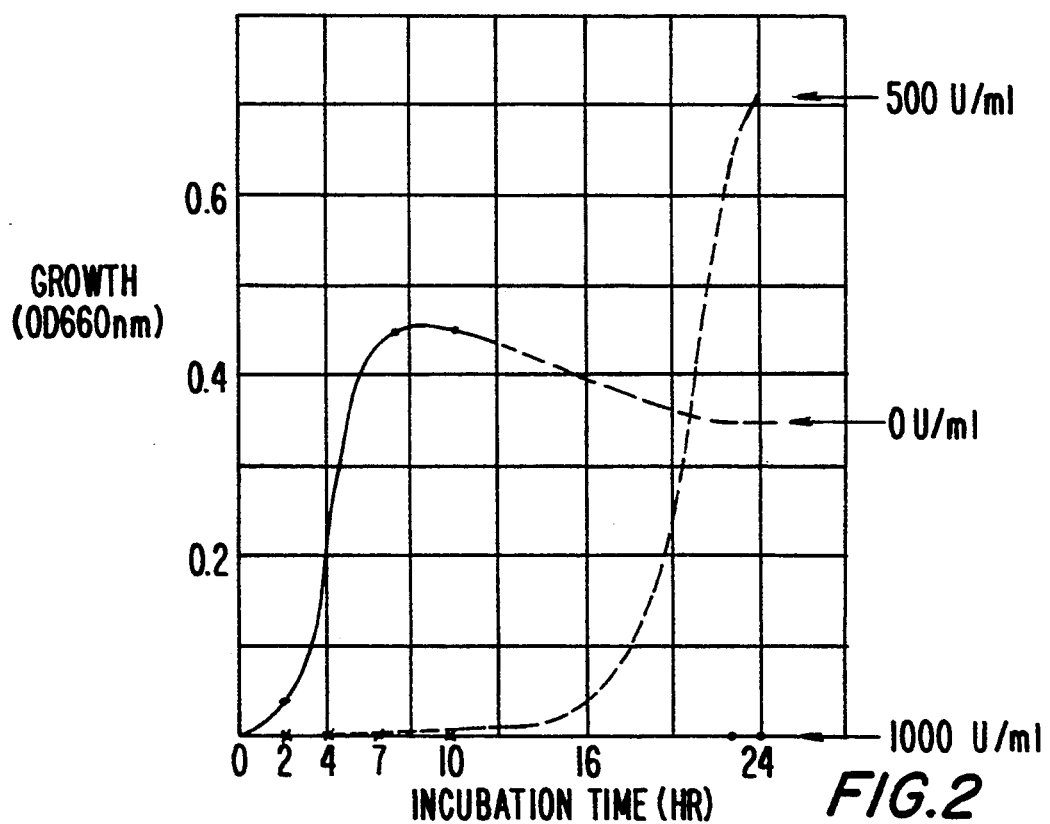

FIG. 2 graphically presents the inhibitory effect of lytic enzyme from strain 391-1 on the growth of *Pseudomonas aeruginosa* (ATCC 9027).

The Microorganisms

The microorganisms of this invention are aerobic, bacillus isolates of *Bacillus pabuli*.

Two strains have been deposited at the Agricultural Research Culture Collection (NRRL), Peoria, Ill., U.S.A., under the terms of the Budapest Treaty, as follows:

| Depositor's reference | 350-2 | 391-1 |
| --- | --- | --- |
| Deposit No. | NRRL B-18446 | NRRL B-18447 |
| Deposit Date | | |
| Taxonomic designation | *Bacillus pabuli* | *Bacillus pabuli* |

Mutants of lytic enzyme producing strains of *B. pabuli*, e.g., of the above two strains or of the type strain, may be made, and such is contemplated within the scope of the invention.

Also contemplated is employment of recombinant DNA techniques to generate a transformant host cell that elaborates the lytic enzyme complex of this invention. Thus, the lytic enzyme complex of this invention is native to *Bacillus pabuli*, but need not be elaborated thereby. The enzyme may be elaborated by transformed host cells of a different microorganism species altogether.

The following characteristics of the two strains were noted:

| Isolate code | 350-2 | 391-1 |
| --- | --- | --- |
| °C. incubation | 30° | 30° |
| Colony morphology | roughly circular, off-white, smooth but not shiny, tenacious. | roughly circular, off-white, smooth shiny, mucoid. |
| Maximum growth | 45° C. | 45° C. |
| Spore shape | Elliptical or Cylindrical | Elliptical or Cylindrical |
| Sporangium distended distinctly | + | + |
| Spore position dominant | central to terminal | central to terminal |
| Intracelluialar globules[a] | — | — |
| Anaerobic growth[a] | — | — |
| Growth in 5% Nacl | — | — |
| Growth in 7% Nacl | — | — |
| Growth in pH 5.7 broth | + | + |
| Acid from glucose[b] | + | + |
| Gas from glucose[b] | — | — |
| VP (acetoin) | — | — |
| Casein decomposition | + | + |
| Gelatin decomposition | + | + |
| Starch hydrolysis | (+) Restricted | (+) Restricted |
| $NO_3^-$ to $NO_2^-$ | + | + |
| Aesculin hydrolysis | + | — |
| Growth in Inositol | + | — |
| Growth in Melibiose | + | — |
| Growth in Beta-Gentiobiose | + | — |

[a] on glucose agar
[b] Peptone water sugar, Andrade's indicator

Acid was produced from the following carbon sources at 30° C.:

Isolate 350-2: glycerol, ribose, D-xylose, galactose, D-glucose, D-fructose, D-mannose, inositol, mannitol, sorbitol, N-acetylglucosamine, cellobiose, maltose, lactose, melibiose, sucrose, trehalose, starch, glycogen, Beta-gentiobiose, D-turanose.

Isolate 391-1: glycerol, ribose, D-xylose, galactose, D-glucose, D-fructose, D-mannose, mannitol, sorbitol, cellobiose, maltose, lactose,sucrose, trehalose, starch, glycogen, D-turanose.

Differences have been found between strain 350-2 and strain 391-1, namely, the reaction on Aesculin hydrolysis and the colony morphology.

Assay for Cell Wall Hydrolitic Activity

The cell wall hydrolytic activity in strain 350-2, strain 391-1 and NRS-924 cultures was determined by the turbidity reduction method (K. Hayashi et. al., Agric. Biol. Chem. 1981. 45(10) :2289). Viable or lyophilized target organisms, *E. coli* ( ATCC 26 ), *Pseudomonas aeruginosa* ( ATCC 9027), *Salmonella arizona* (ATCC 12323) , *Vibrio parahaemolyticus* ( ATCC 35117 ) and *Micrococcus luteus* ( ATCC 4695), are first suspended in 50 mM phosphate buffer, pH 7.0 to an OD at 660 nm of 0.8. To 2 ml of such a cell suspension, 0.5 ml of an appropriately diluted enzyme broth is added and the reaction mixture is incubated at 30° C. for 20 minutes. At the end of incubation time, the decrease in turbidity of the cell suspension at 660 nm ($\Delta$OD 660 nm) is measured by use of a spectrophotometer. One lytic unit is defined as an amount of lytic enzyme which causes a decrease of 0.001 at OD 660 nm in turbidity of cell suspension at 30° C. per minute.

It should be appreciated that measurement of different lytic enzyme complexes against different test microorganisms can be expected to provide widely varying values for cell wall hydrolytic activity species to species, complex to complex. As expected, a high degree of variability has been found to exist. In view of the variability that can be expected, a lytic enzyme from a strain of *Bacillus pabuli* not exemplified herein should be tested against many target microorganisms to ascertain whether its level of effectiveness is adequate for the intended use. It is noted that the numerical values hereinafter provided for the cell wall hydrolytic activity are those measured by the herein described tests. Other tests may result in different numerical values.

Cell count experiments have ascertained that the turbidity decrease of a cell suspension at 660 nm correlates with the actual kill of the target organisms. The procedure is the same as described by K. Hayashi, et. al., supra, except that all solutions excluding the cell suspension are autoclaved and the lytic enzyme solution is filter sterilized. At the end of the incubation, reaction mixtures are serially diluted and plated on nutrient agar plates for survival bacterial counts.

Cell wall hydrolytic activity was also determined by the chemical, enzymatic assays.

(a). N-acetylmuramidase activity is measured by using cell wall of *E. coli* (ATCC 26) as the substrate and following the formation of N-acetylhexosamine (which is released from the cell wall). To 1 ml of *E. coli* cell wall suspension (which contains 1.6 mg cell wall) made in 50 mM MES buffer, pH 6.0, 0.2 ml enzyme solution is added and the reaction mixture is incubated at 37° C. for 30 minutes with shaking. At the end of incubation time, the unused cell wall is removed by centrifugation and the supernatant is used to measure the concentration of released N-acetylhexosamine via p-dimethylaminobenzaldehyde (DMAB) method (J. L. Reissig, et. Biol. Chem. 1955, 217:959–966). One unit is the amount of enzyme which releases 1 nmole N-acetylhexosamine per minute from the cell wall at 37° C.

(b). N-acetylglucosaminidase is assayed with the synthetic substrate P-nitrophenyl-N-acetyl-B-D-glucosaminide (0.5 umole per ml) in 0.05M sodium citrate /citric acid buffer, pH 7.0 at 30° C. (0.05 ml total volume). The amount of substrate hydrolyzed is determined by measuring the absorbance at 415 nm after the enzyme reaction is terminated by addition of 1 ml 0.1M glycine /NaOH buffer, pH 12.5. One unit of N-acetylglucosaminidase is defined as that amount of enzyme which under assay conditions will liberate 1 umole P-nitrophenol within one minute.

As shown in Table I, hereinafter provided, the lytic enzyme complex from *Bacillus pabuli* strain 350-2 (NRRL B-18446) and from strain 391-1 (NRRL B-18447) show excellent lysing activity towards the various target organisms especially toward those of Gram-negative pathogenic bacteria.

Salmonella, Campylobacter, Vibrio, and *E. coli* are recognized foodborne pathogens. Two types of bacterial foodborne disease are recognized: intoxications and infections. Foodborne bacterial intoxication is caused by ingestion of food containing therein bacterial toxin(s) resulting from bacterial growth in the food. Foodborne infection, on the other hand, is caused by ingestion of food containing viable bacteria which then grow and become established in the host, resulting in illness. Some pathogens are present in the intestinal tracts of normal, healthy animals and, in some instances, of man. Certain pathogens are ubiquitous in nature, occurring in soil and vegetation, in animal wastes, and on animal carcasses. Water supplies may contain pathogens when contaminated with fecal matter. Coastal waters in particular may harbor the recently recognized pathogen *Vibrio vulnificus*. Preventing one or more pathogen microoganisms from entering raw foods is very difficult.

The lytic enzyme produced by *Bacillus pabuli* first can be used to inhibit the growth of one or more pathogens on various raw foods, and then to degrade the pathogens already present by lysing their cell walls. As shown in FIG. 1 and Table II, it is clear that at 500 lytic unit per ml of reaction mixture the 391-1 lytic enzyme complex effectively inhibited the growth of *E. coli* (ATCC 26). Furthermore, the inoculum ($10^8$ cells) was completely lysed.

Similar inhibition can be achieved by using *Salmonella arizona* (ATCC 12323) as the test organism. At the dose of 500 lytic unit per ml of reaction mixture, the 391-1 lytic enzyme was able to inhibit 100% growth of *Salmonella arizona* as shown in Table III.

The growth of *Pseudomonas aeruginosa*, an ubiquitous opportunist microoganism, also can be controlled by the 391-1 lytic enzyme, see Table IV and FIG. 2. At the dose of 500 unit/ml, the 391-1 lytic enzyme was able to arrest *Pseudomonas aeruginosa* growth for ~7 hrs. A 99.99% inhibition was achieved at the enzyme dose level of 1000 unit/ml. Note that the lytic unit was assayed by using *E. coli* as the substrate organism.

Preparation of Lytic Enzyme Concentrate

*Bacillus pabuli* strain 350-2 (NRRL B-18446) and strain 391-1 (NRRL B-18447) like the type strain (NRS-924) may be cultivated under aerobic conditions in a nutrient medium containing assimilable carbon and nitrogen together with other essential nutrients, the medium being formulated according to the known art, and per se forms no part of this invention. In addition, the nutrient medium should also contain the usual trace substances.

Suitable carbon sources are carbohydrates, such as sucrose, glucose, and maltose, or carbohydrate containing materials such as cereal grains, malt, rice and sorghum. The carbohydrate concentration incorporated in the medium may vary widely, e.g., 1 to 15%, but usually 8–10% will be suitable, the percentage being calculated as equivalents of glucose.

The nitrogen source in the nutrient medium may be organic or inorganic in nature. Among the suitable organic nitrogen sources, quite a number are regularly used in fermentation processes for the cultivation of bacilli. Illustrative examples are soybean meal, soybean flour, cotton seed meal, cornsteep liquor, and yeast extract.

For aerobic submerged cultivation of the strains in tank fermentors, it is necessary to use artificial aeration. The rate of aeration may be that employed heretofore in conventional tank fermentations.

After fermentation, a liquid enzyme product may be produced from the fermentation broth by no more than removal of coarse material from the broth and, if desired, through concentration of the broth, e.g., evaporation at low temperature or by ultrafiltration. Finally, preservatives may be added to the concentrate.

As has been pointed out, the bacteriolytic enzyme complex of this invention can also be prepared by cultivation of a transformed microorganism cell which is made to contain a gene encoding for and expressing the lytic enzyme complex native to the *Bacillus pabuli*, e.g., to one of the strains herein described, followed by recovery of the lytic enzyme from the culture broth.

Thus, the microorganism to be cultivated is either a lytic enzyme complex producing strain of *Bacillus pabuli* wherein the complex is a native enzyme (including mutants and variants of a wild strain productive of the lytic enzyme complex), or is a transformed host organism wherein the gene for the lytic enzyme complex has been inserted by recombinant DNA techniques. Such techniques are now well known in the art and need not be described herein.

Preferred host organisms are strains of Bacillus and Aspergillus.

Enzyme Preparation

Solid enzyme preparations may be prepared from purified and/or concentrated broth by precipitating the enzyme complex with salts such as $Na_2SO_4$ or with water miscible solvents such as ethanol or acetone. Complete removal of water from the fermentation broth by drying methods such as spray drying, evaporation under vacuum or even lyophilization may also be employed. The hydrolytic activity of lytic enzyme preparations obtained as of the date hereof has usually been about 5000 units/g of powder. This is still a crude product and may be purified if enzyme concentrates of greater unit activity are desired.

Non-dusting granulates containing the lytic enzyme complex may be prepared, e.g. according to U.S. Pat. No. 4,106,991 or 4,661,452, and the granules may be coated according to principles known in the art.

Liquid form lytic enzyme complex preparations may be stabilized, e.g., by addition of propylene glycol, other polyols, sugars, sugar alcohols and boric acid and other enzyme stabilizers known in the art.

For further understanding of the invention, the following specific examples are provided.

EXAMPLE I

*Bacillus pabuli* strain 391-1 (NRRL B-18447) and strain 350-2 (NRRL B-18446) were cultivated at 30° C. on a rotary shaking table (250 rpm) in 250 ml triple-baffled Erlenmeyer flasks containing 50 ml of medium of the following composition:

Composition of the medium in grams per liter:

| | |
|---|---|
| soybean flour | 10 |
| $K_2HPO_4$ | 1 |
| $MgSO_4 \cdot 7H_2O$ | 1 |
| yeast extract | 1 |

No pH adjustment was required.

After 12 to 16 hrs of incubation, the lytic enzyme activity of the broth was determined by using the turbidity reduction method described above. The lytic activities of the strain 391-1 broth and 350-2 broth were 49 unit/ml and 40 unit/ml respectively when lytic. *E. coli* (ATCC 26) was used as the target substrate organism.

EXAMPLE II

A multiplicity of microorganisms, including some known to be pathogens, opportunists and difficult to lyse by egg-white lysozyme, were tested in pure culture as the substrate organisms for both strain 350-2 lytic enzyme and strain 391-1 lytic enzyme. Llytic enzyme was dosed at 8 lytic unit per ml of reaction mixture (using *E. coli* (ATCC 26) as the target substrate) and assayed as described in the text. The % of lysis was calculated as follows:

$$\% \text{ lysis} = \frac{OD_{660} \text{ of untreated} - OD_{660} \text{ of treated sample}}{OD_{660} \text{ of untreated}} \times 100$$

As shown in Table I, both 350-2 and 391-1 lytic enzymes lyse Gram-negative bacteria very effectively. However, lytic enzyme from 350-2 and lytic enzyme from 391-1 do show differences in preferred target organisms.

TABLE I

| SUBSTRATE ORGANISM | 350-2 LYTIC ENZYME (% LYSIS) | 391-1 LYTIC ENZYME (% LYSIS) |
|---|---|---|
| Gram-negative | | |
| E. coli (ATCC 26) | 65 | 82 |
| E. coli (NOVO) | 22 | 87 |
| Pseudomonas aeruginosa (ATCC 9027) | 66 | 56 |
| Serratia marcescens (QMB 1466) | 45 | 33 |
| Salmonella arizona (ATCC 12323) | 71 | 65 |
| Vibrio darahaemolyticus (ATCC 35117) | 47 | 43 |
| Campylobacter fetus (ATCC 27374) | 11 | 10 |
| Gram-postive | | |
| Bacillus subtilis (ATCC 6633) | 28 | 41 |
| Corynebacterium liquefaciens (ATCC 14929) | 34 | 50 |
| Micrococcus luteus (ATCC 4698) | 25 | 71 |

*E. coli (NOVO) is an E. coli isolate which was isolated from chicken feces.

EXAMPLE III

The antibacterial activity of the 391-1 lytic enzyme towards a growing culture of *E coli* (ATCC 26) was determined by using the method described by T. Miyamato, et. al., (J. Food Hyg. Soc. Japan. Vol. 28, P. 364-371, 1987).

Approximately $10^8$ cells of overnight grown *E. coli* (in 0.5 ml volume) were inoculated into 10 ml of reaction mixture which contained 5 ml of Nutrient Broth, 1 mi of filter-sterilized 391-1 lytic enzyme (about 5000 lytic unit/ml) and 3.5 ml of sterile water. The mixture was cultured at 30° C. for 24 hours with 200 rpm shaking. The *E coli* growth was monitored as shown in Table II by measuring the change in absorbance at 660 nm. At the end of 24 hours incubation, culture broths were serially diluted and plated onto Nutrient Agar plates and incubated overnight to obtain the actual CFU counts. The 391-1 lytic enzyme activity (lytic unit/ml) was assayed by using *E. coli* (ATCC 26) as the substrate.

TABLE II

| Dose of Enzyme | Growth($OD_{660}$) | | | | plate count at 24 hr |
|---|---|---|---|---|---|
| | 0 hr | 7 hr | 12 hr | 24 hr | |
| 0 u/ml | 0.016 | 0.490 | 0.523 | 0.574 | $8.8 \times 10^8$ CFU/ml |
| 500 u/ml | 0.029 | 0.015 | 0.018 | 0.019 | 0 |

391-1 lytic enzyme effectively inhibited the growth of *E. coli* at the dose of 500 unit/ml. Furthermore, at the end of 24 hours incubation, the inoculum ($10^8$ cells) was completely lysed.

EXAMPLE IV

An antibacterial effect of the 391-1 lytic enzyme on growth of *Salmonella arizona* (ATCC 12323) was ascertained, using the method described in Example III.

*S. arizona* was cultivated with and without the lytic enzyme at 25° C. (the best temperature for *S. arizona* to grow) for 24 hours with 200 rpm shaking. Nutrient Broth was the medium used in the experiment. 391-1 lytic enzyme activity (unit/ml) was assayed with *E. coli* as the substrate.

It is evident in Table III, at the dose of 500 unit/ml that 391-1 lytic enzyme was able to inhibit by 100% the growth of *S. arizona*. Similar to the effect of 391-1 lytic enzyme on *E. coli*, the original inoculum ($10^8$ cells) of *S. arizona* was also completely lysed.

TABLE III

| Dose of Enzyme | Growth($OD_{660}$) | | | | plate count at 24 hr |
|---|---|---|---|---|---|
| | 0 hr | 4 hr | 0.5 hr | 24 hr | |
| 0 u/ml | 0.014 | 0.105 | 0.348 | 0.461 | $1.1 \times 10^9$ CFU/ml |
| 500 u/ml | 0.025 | 0.015 | 0.014 | 0.013 | 0 |

EXAMPLE V

The antibacterial effect of 391-1 lytic enzyme on growth of *Pseudomonas aeruginosa* (ATCC 9027) was ascertained using the method described in Example III.

*P. aeruginosa* was cultivated with and without the enzyme at 30° C. for 24 hours with 200 rpm shaking. Nutrient Broth was the medium used in the experiment. 391-1 lytic enzyme activity (unit/ml) was assayed with *E. coli* as the substrate.

As shown in Table IV, at the dose of 500 unit/ml, 391-1 lytic enzyme was only able to arrest *P. aeruginosa* growth for about 7 hours. At the dose of 1000 unit/ml anti for 24 hours incubation (as shown in FIG. 2), 391-1 lytic enzyme achieved 99.99% growth inhibition of the organism.

TABLE IV

| Dose of Enzyme | Growth($OD_{660}$) | | | | plate count at 24 hr |
|---|---|---|---|---|---|
| | 0 hr | 4 hr | 10 hr | 24 hr | |
| 0 u/ml | 0.013 | 0.190 | 0.465 | 0.367 | $1.8 \times 10^9$ CFU/ml |
| 500 u/ml | 0.024 | 0.025 | 0.035 | 0.622 | $1.1 \times 10^9$ CFU/ml |
| 1000 u/ml | 0.039 | 0.031 | 0.028 | 0.028 | $1.9 \times 10^5$ CFU/ml |

The better growth (higher $OD_{660}$) observed for the 500 u/ml sample at 24 hour time point is believed attributable to the extra-nutrient present in the enzyme solution added into the reaction mixture.

We claim:

1. A substantially purified bacteriolytic enzyme preparation derived from a strain of *Bacillus pabuli* which has:
   (a) a pH optimum of 6.0,
   (b) a temperature optimum in the range of 50–60° C., and
   (c) the ability to hydrolyze bacterial cell walls of *Vibrio parahaemolyticus, Salmonella arizona, Campylobacter fetus, Pseudomonas aeruginosa, Serratia marcescens, Corynebacterium, liquefaciens* and *Micrococcus luteus*.

2. The bacteriolytic enzyme preparation according to claim 1, wherein the strain is NRRL B-18447 or a mutant thereof productive of the bacteriolytic enzyme.

3. A substantially purified bacteriolytic enzyme preparation which has the ability to hydrolyze bacterial cell walls of *Vibrio parahaemolyticus, Salmonella arizona, Campylobacter fetus, Pseudomonas aeruginosa, Serratia marcescens, Corynebacterium liquefaciens* and *Micrococcus luteus* and is derived from *Bacillus pabuli* NRRL B-18446 or a mutant thereof productive of the bacteriolytic enzyme.

4. A substantially purified bacteriolytic enzyme preparation which has the ability to hydrolyze bacterial cell walls of *Vibrio parahaemolyticus, Salmonella arizona, Campylobacter fetus, Pseudomonas aeruginosa, Serratia marcescens, Corynebacterium liquefaciens* and *Micrococcus luteus* and is derived from *Bacillus pabuli* NRRL NRS-924 or a mutant thereof productive of the bacteriolytic enzyme.

* * * * *